(12) United States Patent
Cagnac et al.

(10) Patent No.: US 11,560,542 B2
(45) Date of Patent: Jan. 24, 2023

(54) PROCESS FOR PRODUCING PHYCOCYANIN-RICH BIOMASS VIA URA CULTURING

(71) Applicant: FERMENTALG, Libourne (FR)

(72) Inventors: Olivier Cagnac, Libourne (FR); Axel Athane, Carbon Blanc (FR); Marion Champeaud, Langoiran (FR)

(73) Assignee: FERMENTALG, Libourne (FR)

( * ) Notice: Subject to any disclaimer, the term of this patent is extended or adjusted under 35 U.S.C. 154(b) by 0 days.

(21) Appl. No.: 17/059,979

(22) PCT Filed: May 27, 2019

(86) PCT No.: PCT/EP2019/063578
§ 371 (c)(1),
(2) Date: Nov. 30, 2020

(87) PCT Pub. No.: WO2019/228947
PCT Pub. Date: Dec. 5, 2019

(65) Prior Publication Data
US 2021/0230534 A1    Jul. 29, 2021

(30) Foreign Application Priority Data
May 31, 2018 (FR) ........................... 1800537

(51) Int. Cl.
| | |
|---|---|
| *A61K 38/00* | (2006.01) |
| *C12N 1/12* | (2006.01) |
| *A23L 5/46* | (2016.01) |
| *A01G 33/00* | (2006.01) |
| *C12P 21/02* | (2006.01) |

(52) U.S. Cl.
CPC .............. *C12N 1/12* (2013.01); *A01G 33/00* (2013.01); *A23L 5/46* (2016.08); *C12P 21/02* (2013.01); *A23V 2002/00* (2013.01); *C12N 2500/34* (2013.01)

(58) Field of Classification Search
None
See application file for complete search history.

(56) References Cited

U.S. PATENT DOCUMENTS

2021/0230534 A1*  7/2021  Cagnac ................. C07K 14/405

FOREIGN PATENT DOCUMENTS

| | | |
|---|---|---|
| FR | 2789399 A1 | 8/2000 |
| FR | 3064635 A1 | 10/2018 |
| WO | 2017/050917 A1 | 3/2017 |
| WO | 2017/050918 A1 | 3/2017 |
| WO | 2017/093345 A1 | 6/2017 |
| WO | 2018/178334 A1 | 10/2018 |

OTHER PUBLICATIONS

Heredia-Arroyo, Tamarys, "Mixotrophic cultivation of Chlorella vulgaris and its potential application for the oil accumulation from non-sugar materials", Biomass and Bioenergy 35, 2011, 2245-2253.
Carfagna, Simona, "Different characteristics of C-phycocyanin (C-PC) in two strains of the extremophilic Galdieria phlegrea", Algal Research 31, 2018, 406-412.
Jaouen et al., "Clarification and concenlialion with membrane technology of a phycocyanin solution extracted from Spirulina platensis", Biotechnology Techniques 13, 1999, 877-881.
Oesterhelt, Christine et al., "Regulation of photosynthesis in the unicellular acidophilic red alga Galdieria sulphuraria", The Plant Journal 51, 2007, 500-511.
Stadnichuk et al., "Ininhibition by glucose of chlorophyll a and phycocyanobilin biosynthesis in the unicellular red alga Galdieria partita at the stage of coproporphyrinogen III formation", Plant Science 136, 1998, 11-23.
Gross et al., "Heterotrophic Growth of Two Strains of the Acido-Thermophilic Red Alga Galdieria sulphuraria", Plant Cell Physiol. 36(4), 1995, 633-638.
Moon et al., "Isolation and characterization of thermostable phycocyanin from Galdieria sulphuraria", Korean J. Chem. Eng., 31(3), 2014, 490-495.
Sloth et al., "Accumulation of phycocyanin in heterotrophic and mixotrophic cultures of the acidophilic red alga Galdieria sulphuraria", Enzyme and Microbial Technology 38, 2006, 168-175.
International Search Report of PCT/EP2019/063578, Search completed on Jul. 8, 2019, Robert Lejeune.

* cited by examiner

*Primary Examiner* — Hope A Robinson
(74) *Attorney, Agent, or Firm* — BCF LLP

(57) ABSTRACT

The invention relates to the cultivation of unicellular red algae (URA) for producing biomass for the production of products of interest, such as dry biomass or compounds or mixtures of compounds of interest extracted from the biomass produced, particularly food pigments or colouring agents. The invention more particularly relates to the industrial production of said biomass, which must satisfy an economic equilibrium of profitability, with both an increase in productivity (quantity of biomass and of compounds of interest in the biomass) and an economically acceptable production cost.

17 Claims, 1 Drawing Sheet

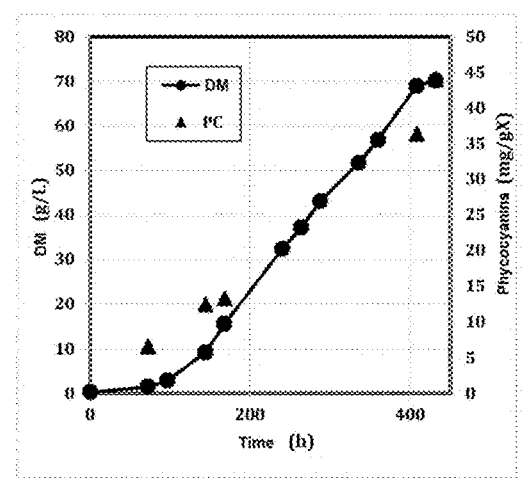

PROCESS FOR PRODUCING PHYCOCYANIN-RICH BIOMASS VIA URA CULTURING

CROSS-REFERENCE TO RELATED APPLICATIONS

This application is a national phase filing under 35 U.S.C. 371 of International Application No. PCT/EP2019//063578, filed on May 27, 2019, which claims the benefit of FR Patent Application No. FR 1800537, filed on May 31, 2018. The contents of the aforementioned applications are incorporated by reference in their entirety herein.

FIELD OF THE INVENTION

The present invention relates to the cultivation of URA for the production of biomass with a view to the production of products of interest, such as dried biomass or compounds or mixtures of compounds of interest extracted from the biomass produced, in particular food pigments or dyes. The invention relates more particularly to the industrial production of this biomass, which must meet an economic balance of profitability with, on the one hand, an increase in productivity (amount of biomass and compounds of interest in the biomass) and, on the other hand, an economically acceptable production cost.

PRIOR ART

Phycocyanins are pigments produced by unicellular microorganisms that can be used for coloring foods. Today, they are mainly produced by the culture of cyanobacteria, in ponds and autotrophically, with a low yield of produced biomass. To increase the production of these phycocyanins, a search has been made for phycocyanin-producing species that can be cultivated under bioreactor fermentation conditions in order to increase the amount of biomass produced.

Unicellular red algae (URA) belonging to the class Cyanidiophyceae such as *Galdieria sulphuraria* are known to produce phycocyanins (Carfagna et al., 2018) capable of growing under autotrophic, mixotrophic and heterotrophic conditions. The addition of one or more carbon sources in the culture medium can significantly increase the growth rate. These microalgae are able to consume a large number of carbon metabolites, in total more than 30 have been counted (glucose, glycerol, pentose . . . ) (Gross et al., 1995; Oesterhelt et al., 1999-2007; Sloth et al., 2006). However, despite faster growth, the cellular phycocyanins content is much lower under heterotrophic and mixotrophic conditions than under autotrophic conditions. The addition of a carbon source in the culture medium—in the presence or absence of light—strongly suppresses phycocyanin production (Stadnichuk et al., 1998).

To compensate for this decrease in intrinsic phycocyanin production, culture methods have been developed to increase the cell density in the fermenters and the amount of dry matter produced. By increasing dry matter, the amount of phycocyanin produced is also increased (WO 2017/050917, WO 2017/093345). It is also possible, depending on the URA used, to produce phycocyanins with new properties, such as better stability at acidic pH (WO 2017/050918, FR 3 064 365 and WO 2018/178334).

An improvement of these production processes would combine both the advantages of industrial production by fermentation on carbon substrate, while reducing the suppression of phycocyanin production associated with the carbon source.

DISCLOSURE OF THE INVENTION

The present invention relates to a novel process for cultivating unicellular red algae (URA) for the production of a phycocyanin-rich biomass, comprising the steps of (i) culturing said URA in mixotrophic or heterotrophic mode on a culture medium comprising a carbon source comprising glucose, and (ii) recovering the biomass, characterized in that an amount of glycerol sufficient to increase phycocyanin production compared with the glycerol-free culture is added to the culture medium.

The invention also relates to a process for preparing phycocyanins which comprises the production of a biomass according to the invention and a step (iii) of extracting the phycocyanins from the previously recovered biomass.

DESCRIPTION OF THE FIGURES

FIG. 1 shows the phycocyanin growth and production monitoring curves under the growing conditions of Example 1.

DETAILED DESCRIPTION OF THE INVENTION

The present invention relates to a novel process for cultivating unicellular red algae (URA) for the production of a phycocyanin-rich biomass, comprising the steps of (i) culturing said URA in mixotrophic or heterotrophic mode on a culture medium comprising a carbon source comprising glucose, and (ii) recovering the biomass, characterized in that an amount of glycerol sufficient to increase phycocyanin production compared with the glycerol-free culture is added to the culture medium.

The URA used to produce biomass by fermentation and the fermentation methods, especially for the production of phycocyanins, are well known to the person skilled in the art. In particular, mention may be made of patent applications WO 2017/050917, WO 2017/093345, WO 2017/050918 and FR 1752674 filed on 30 Mar. 2017.

The URA are in particular selected from the subdivision Cyanidiophytina, in particular from the class Cyanidiophyceae, more particularly from the order Cyanidiales, even more particularly selected from the families Cyanidiaceae or Galdieraceae. Preferably, the URA are selected from the genera Cyanidioschyzon, Cyanidium or Galdieria. More preferentially, the URA employed in the process according to the invention are selected from the species *Cyanidioschyzon morulae* 10D, *Cyanidioschyzon merolae* DBV201, *Cyanidium caldarium*, *Cyanidium daedalum*, *Cyanidium maximum*, *Cyanidium partitum*, *Cyanidium rumpens*, *Galdieria daedala*, *Galdieria maxima*, *Galdieria partita* or *Galdieria sulphuraria*.

The culture media used in the process according to the invention are well known to the skilled person, in particular described in patent applications WO 2017/050917, WO 2017/093345, WO 2017/050918 and FR 1752674 filed on 30 Mar. 2017.

These culture media comprise a carbon source comprising glucose. It may be glucose or glucose in a complex form such as lactose, fructose, or glucose-containing polysaccharides.

This carbon source can come from the sugar, beet or cane industry, starch hydrolysates from starchy plants such as corn, wheat, potato, or from the dairy industry such as milk permeate (WO 2017/093345), rich in lactose, used alone or in mixture.

Advantageously, the carbon source comprising glucose is selected from glucose and lactose.

The culture medium generally comprises the carbon source comprising glucose in an amount comprised between 0.05 g/L and 200 g/L, advantageously between 1 g/L and 150 g/L, very advantageously between 10 g/L and 80 g/L.

The culture medium may comprise other elements well known to the skilled person in the field of microalgae culture by fermentation, in particular a source of phosphorus and/or a source of nitrogen, and/or a source of sulfur.

According to the invention, the sources of phosphorus may be selected from the following species: phosphoric acid, phosphorus salts, advantageously sodium hydrogen phosphorus ($Na_2HPO_4$), or sodium dihydrogen phosphorus ($NaH_2PO_4$), or potassium dihydrogen phosphorus ($KH_2PO_4$), or potassium hydrogen phosphorus ($K_2HPO_4$), or any mixture, in any proportion of at least two of these sources.

The medium may also comprise macroelements and microelements that promote the cultivation of URA.

The illumination conditions for mixotrophic mode cultivation of URA are also known to the skilled person, in particular described in patent applications WO 2017/050917, WO 2017/050918, WO 2017/093345 and FR 1752674 filed on 30 Mar. 2017.

Illumination can be continuous or discontinuous, particularly discontinuous in the form of flashes. According to a particular embodiment, the illumination is carried out with blue light (WO 2017/050917), more particularly in the form of a radiation having a narrow spectrum of wavelength comprised between 400 and 550 nm, advantageously a narrow spectrum of wavelength comprised between 420 nm and 500 nm, advantageously between 430 and 480 nm, very preferentially centered on 455 nm.

The invention is characterized by the fact that glycerol is added to the culture medium in an amount sufficient to increase the production of phycocyanins compared with the glycerol-free culture.

This addition can be done in the culture medium at the beginning of the culture, or in the middle of the culture, once the biomass has reached a determined density, for example greater than 20 g/L dry matter in the culture medium.

The culture step (i) can thus be split into two substeps, (ia) growth to produce biomass with a carbon source essentially comprising glucose in a simple or complex form as defined above and (ib) accumulation with the addition of glycerol to promote phycocyanin production.

The industrial glycerol sources that can be integrated into the production processes have no restrictions on purity or refining (generally comprised between 80% and 100%). Preferably they are food grade. Suppliers of glycerol sources are well known, particularly those in the biodiesel industry such as the Avril group with Oléon (Glycerine 4808/4808K, Glycerine 4827/4827K . . . ), or the company Cargill which also offers a wide range of glycerol products refined between 86.5% and 99.7% with kosher, halal, RSPO, E442 or GMO-free certifications, in particular.

The carbon source comprising glucose is the main source of carbon in the culture medium and the amount of glycerol sufficient to increase phycocyanin production compared with the glycerol-free culture will be easily determined by the skilled person by simple experimentation in fermenters to compare the amount of phycocyanin produced with or without glycerol as shown in the examples.

The desired increase in phycocyanin production will preferentially be at least 0.15 mg/g/h, more preferentially at least 0.30 mg/g/h, even more preferentially at least 1 mg/g/h; or at least 3.6 mg/g, more preferentially at least 7.2 mg/g, even more preferentially at least 24 mg/gX.

In general, the amount of glycerol added to the culture medium is sufficient to have a weight ratio of glycerol to carbon source comprising glucose (hereinafter identified as Gly/Glu) of at least 1/15. Preferentially the Gly/Glu ratio is at least 1/14, more preferentially at least 1/10, even more preferentially at least 1/5.

The interest being to ensure an optimum profitability between the cost of raw materials and the production of phycocyanin, it will be advantageous not to exceed a Gly/Glu ratio of 1/1.

According to a preferred embodiment of the invention, glycerol is added to the culture medium at a Gly/Glu weight ratio of 1/10 to 1/1, preferentially 1/7 to 1/2, more preferentially about 1/5 to about 1/3.

The process according to the invention may further comprise a biomass recovery step. Said biomass recovery may be carried out by any technique allowing the recovery of the biomass, in particular methods of gravimetric or reduced pressure filtration, of decantation, or precipitation methods followed by gravimetric filtration.

The invention also relates to the biomass obtainable by any of the variants of the process according to the invention.

According to the invention, "biomass" is advantageously understood to mean a set of microorganism cells produced by the culture of these microorganisms, which may or may not have retained their physical integrity. It is therefore understood that said biomass can include an amount of degraded microorganism cells from 0% to 100%. "Degraded" means that the physical integrity of said microorganism cells may have been altered, such as lysed microorganisms for example from a homogenization or enzymatic lysis process. Once produced, this biomass can be raw, just separated from its culture medium, dried or not, degraded or not.

The biomass, depending on whether it is dried or not, totally or partially, can have a moisture content of 1% to 90%.

According to a first embodiment, the biomass has a moisture content of 70% to 90%, preferentially 80% to 85%. This is particularly the case when it is essentially made up of industrial, optimized and cultivated microorganisms, after filtration of the fermentation must to separate the cultivated microorganisms from the culture medium, before drying.

According to another embodiment of the invention, the biomass is dried, totally or partially, and has a moisture content of 1% to 10%, preferentially 2% to 7%. According to the invention, said biomass may have a URA density comprised between 20 and 200 g/L dry matter, preferentially between 90 and 150 g/L dry matter.

According to the invention, said biomass may have an amount of proteins comprised between 25% and 60%, or even up to 70%, preferably between 30% and 55%, more preferentially between 40% and 50% of the dry matter weight. Nitrogen determination and calculation of the crude protein content are carried out according to the block digestion and steam distillation method (NF EN ISO 5983-2).

According to the invention, said biomass may have an intracellular phycobiliprotein (phycocyanin and allophycocyanin) content comprised between 1 and 250 mg/g dry matter, preferentially between 20 and 150 mg/g dry matter.

According to the invention, said biomass may have an intracellular phycocyanin content of between 0.5 and 100 mg/g dry matter, preferably between 10 and 40 mg/g dry matter.

The biomass may be packaged for storage or for use as such, for example as a food supplement or food for human or animal consumption.

The cake obtainable after extraction of phycocyanin from the biomass of URA obtainable by the process according to the invention can be used as a protein- and carotenoid-rich food supplement for human or animal consumption.

According to the invention, said biomass may have an intracellular carotenoid content comprised between 0.1 and 10 mg/g dry matter, advantageously between 0.250 and 1 mg/g dry matter.

URA have a significant potential for use in many fields, including for example food for human or animal consumption, cosmetics and medicine.

According to the invention, said biomass of URA obtainable according to the invention can be used after harvesting either directly, possibly dried, or after processing. In particular, said biomass can be used in the form of flours in food compositions or in the form of food supplements.

The biomass of URA obtainable according to the invention can be processed into flour by any process known to the skilled person. It can thus be envisaged for example that the URA can be separated from the culture medium, lysed and reduced to fine particles (average diameter of 10 microns), then dried.

The invention also relates to any use of the biomass of URA obtainable according to the invention in any known field of use of URA, particularly, food for human or animal consumption, cosmetics, medicine. In the fields of food for human or animal consumption and of cosmetics, it is obviously a matter of non-therapeutic uses intended for healthy animals or human beings.

The biomass obtained after the cultivation of URA according to the process of the invention can be used to obtain in particular a flour rich in antioxidant agents, in particular carotenoids (particularly zeaxanthin and β-carotenes) in contents comprised between 0.1 and 10 mg/g dry matter, advantageously between 0.25 and 1 mg/g dry matter, including in particular zeaxanthin in a content comprised between 0.05 and 5 mg/g dry matter, advantageously between 0.1 and 1 mg/g dry matter, and/or β-carotene in a content of 0.05 and 5 mg/g dry matter, advantageously between 0.1 and 1 mg/g dry matter, meeting a need particularly in the food industry because it is more palatable, has better taste, provides antioxidants in significant amounts and can be used in animal or human food.

The invention therefore relates to a flour obtainable after transformation of biomass into URA obtainable by the process according to the invention.

Whatever the form of use of the product obtainable by the process according to the invention (native or transformed biomass), said product may be used pure or mixed with other ingredients conventionally used, particularly in non-therapeutic uses in food or cosmetics.

The invention also relates to any product that may comprise at least the biomass of algae obtainable according to the invention. The invention also relates to any product that may comprise at least the flour resulting from the transformation of the biomass of algae obtainable according to the invention.

According to the invention, the phycocyanins produced by said biomass can be extracted to be used for example in food or as a dye. The extraction of phycobiliproteins, and particularly of phycocyanin, from said biomass can be carried out according to any extraction technique known to the skilled person, such as, for example, that described by Moon et al. (2014) or by Jaouen et al. (1999) or in applications FR 2 789 399, WO 2017/093345 and FR 1752674 filed on 30 Mar. 2017.

The invention also relates to the use of phycocyanin obtainable according to the process of the invention, in food for animal or human consumption, as a food supplement, or as a dye, particularly as a food dye.

It also relates to a food comprising the phycocyanin obtained by the process according to the invention, in particular a beverage, more particularly a carbonated beverage.

EXAMPLES

Example 1: Comparative Growth of the *G. sulphuraria* Strain on Glycerol, Glucose and a Glucose-Glycerol Mixture The growth of the strain is achieved by measuring the absorbance at 800 nm over time. The culture medium is the one known for this strain (Gross medium), the only difference between the three tested media is the carbon substrate (s) used.

M&M:

Strain: *Galdieria sulphuraria* (also called *Cyanidium caldarium*) UTEX #2919

Culture Medium:

30 g/L glucose or 30 g/L glycerol (glycerine 4808 Univar) or 25 g/L glucose+5 g/L glycerol; 8 g/L (NH4)2SO4; 0.25 g/L KH2PO4; 716 mg/L MgSO4; 44 mg/L CaCl2); 3 mL/L Fe-EDTA stock solution (6.9 g/L FeSO4 and 9.3 g/L Na2-EDTA) and 4 mL trace metal stock solution (3.09 g/L Na2-EDTA; 0.08 g/L CuSO4, 5H2O; 2.86 g/L H3BO3; 0.04 g/L NaVO3, 4H2O; 1.82 g/L MnCl2; 0.04 g/L CoCl2, 6H2O; 0.22 g/L ZnSO4, 7H2O; 0.017 g/L Na$_2$SeO3; 0.03 g/L (NH4)6Mo7O24, 4H2O).

Culture Conditions:

The cultures are carried out on a shaking table (140 rpm) in a thermostatically controlled chamber at 37° C., in a medium as described above in the presence of a light source.

Culture Monitoring:

Growth monitoring shows that similar ODs are achieved regardless of the carbon source(s) used. The dry masses and the associated phycocyanin determinations after 312 h of cultivation are described in the table.

| Substrate(s) used | Dry mass (g/L) | Phycocyanin (mg/gX) | Productivity (mg/L/h) |
|---|---|---|---|
| Glucose | 18.8 | 14.17 ± 0.51 | 0.853 |
| Glycerol | 19.7 | 42.02 ± 0.95 | 2.65 |
| Glucose + Glycerol | 17.47 | 51.64 ± 0.04 | 2.9 |

The addition of glycerol to the medium activates phycocyanin production despite the presence of glucose known as a phycocyanin inhibitor.

Example 2: Comparative Growth of the *G. sulphuraria* Strain on Milk Permeate and a Milk Permeate-Glycerol Mixture The growth of the strain is determined by measuring the absorbance at 800 nm over time. The culture medium is that known for this strain (Gross medium), the only difference between the two tested media is the carbon substrate(s) used.

M&M:

Strain: *Galdieria sulphuraria* (also called *Cyanidium caldarium*) UTEX #2919

Culture Medium:

30 g/L milk permeate or 25 g/L milk permeate+5 g/L glycerol (glycerine 4808 Univar); 8 g/L (NH4)2SO4; 0.25 g/L KH2PO4; 716 mg/L MgSO4; 44 mg/L CaCl2); 3 mL/L Fe-EDTA stock solution (6.9 g/L FeSO4 and 9.3 g/L Na2-EDTA) and 4 mL trace metal stock solution (3.09 g/L Na2-EDTA; 0.08 g/L CuSO4, 5H2O; 2.86 g/L H3B03; 0.04 g/L NaVO3, 4H2O; 1.82 g/L MnCl2; 0.04 g/L CoCl2, 6H2O; 0.22 g/L ZnSO4, 7H2O; 0.017 g/L Na2SeO3; 0.03 g/L (NH4)6Mo7O24, 4H2O).

Culture Conditions:

The cultures are carried out on a shaking table (140 rpm) in a thermostatically controlled chamber at 37° C., in a medium as described above in the presence or absence of a light source.

Culture Monitoring:

The dry masses and associated phycocyanin determinations after 168 hours of cultivation are described in Table 2(A) in the presence of light and in Table 2(B) in the dark.

| 2(A) Mixotrophy | | | |
|---|---|---|---|
| Substrate(s) used | Dry mass (g/L) | Phycocyanin (mg/gX) | Productivity (mg/L/h) |
| Milk permeate | 13.6 ± 0.31 | 7.983 ± 0.36 | 0.65 |
| Milk permeate + Glycerol | 10.93 ± 0.16 | 21.153 ± 0.88 | 1.38 |

| 2(B) Heterotrophy | | | |
|---|---|---|---|
| Substrate(s) used | Dry mass (g/L) | Phycocyanin (mg/gX) | Productivity (mg/L/h) |
| Milk permeate | 12.03 ± 0.07 | 3.54 ± 0.11 | 0.25 |
| Milk permeate + Glycerol | 8.81 ± 0.37 | 6.11 ± 0.15 | 0.32 |

The addition of glycerol to the medium activates phycocyanin production despite the presence of the phycocyanin-inhibiting milk permeate and this increase in production is noticeable even in the dark.

Example 3: Monitoring of a Process for Bioreactor Culture of the *G. sulphuraria* Strain on a Glucose-Glycerol Mixture The growth of the strain is monitored by measuring the dry mass over time and substrate consumption is identified by HPLC assay. An intracellular phycocyanin determination is also performed over time. The culture medium is that known for this strain (Gross medium) with a substrate of ⅙ glycerol and ⅚ glucose for the starter and a feed composed of ¼ glycerol and ¾ glucose for the fed-batch.

M&M:

Strain: *Galdieria sulphuraria* (also called *Cyanidium caldarium*) UTEX #2919 Culture medium:

Starter:

25 g/L glucose+5 g/L glycerol (glycerine 4808 Univar); 8 g/L (NH4)2SO4; 0.25 g/L KH2PO4; 716 mg/L MgSO4; 44 mg/L CaCl2); 3 mL/L Fe-EDTA stock solution (6.9 g/L FeSO4 and 9.3 g/L Na2-EDTA) and 4 mL trace metal stock solution (3.09 g/L Na2-EDTA; 0.08 g/L CuSO4, 5H2O; 2.86 g/L H3BO3; 0.04 g/L NaVO3, 4H2O; 1.82 g/L MnCl2; 0.04 g/L CoCl2, 6H2O; 0.22 g/L ZnSO4, 7H2O; 0.017 g/L Na2SeO3; 0.03 g/L (NH4)6Mo7O24, 4H2O). Fed-batch medium: 375 g/L glucose+125 g/L glycerol (glycerine 4808 Univar); 20 g/L (NH4)2SO4; 4.17 g/L KH2PO4; 5.96 g/L MgSO4; 0.37 g/L CaCl2; 25 mL/L Fe-EDTA stock solution (6.9 g/L FeSO4 and 9.3 g/L Na2-EDTA) and 33 mL trace metal stock solution (3.09 g/L Na2-EDTA; 0.08 g/L CuSO4, 5H2O; 2.86 g/L H3BO3; 0.04 g/L NaVO3, 4H2O; 1.82 g/L MnCl2; 0.04 g/L CoCl2, 6H2O; 0.22 g/L ZnSO4, 7H2O; 0.017 g/L Na2SeO3; 0.03 g/L (NH4)6Mo7O24, 4H2O).

Culture Conditions:

Cultures are carried out in a 2 L bioreactor at a regulated temperature of 37° C., pH 3, in the presence of a light source.

Growth monitoring shows that a dry mass of 70 g/L is reached after 427 h of culture and an intracellular phycocyanin content of 45 mg/gX (FIG. 1). All the carbon substrate provided is consumed.

Example 4: Monitoring of a Process for Bioreactor Culture of the *G. sulphuraria* Strain on a Milk Permeate-Glycerol Mixture The growth of the strain is monitored by measuring the dry mass over time and the substrate consumption is identified by HPLC assay. An intracellular phycocyanin determination is also performed over time. The culture medium is that known for this strain (Gross medium) with for substrate ⅙ glycerol and ⅚ lactose (provided by the milk permeate) for the starter and a feed composed of ¼ glycerol and ¾ lactose for the fed-batch.

M&M:

Strain: *Galdieria sulphuraria* (also called *Cyanidium caldarium*) UTEX #2919

Culture Medium:

Starter:

25 g/L milk permeate+5 g/L glycerol (glycerine 4808 Univar); 8 g/L (NH4)2504; 716 mg/L MgSO4; 3 mL/L Fe-EDTA stock solution (6.9 g/L FeSO4 and 9.3 g/L Na2-EDTA) and 4 mL trace metal stock solution (3.09 g/L Na2-EDTA; 0.08 g/L CuSO4, 5H2O; 2.86 g/L H3BO3; 0.04 g/L NaVO3, 4H2O; 1.82 g/L MnCl2; 0.04 g/L CoCl2, 6H2O; 0.22 g/L ZnSO4, 7H2O; 0.017 g/L Na2SeO3; 0.03 g/L (NH4)6Mo7O24, 4H2O).

Fed-Batch Medium:

85 g/L milk permeate; 28.3 g/L glycerol

Culture Conditions:

Cultures are carried out in a 2 L bioreactor at a regulated temperature of 37° C., pH 3, in the presence of a light source.

Growth monitoring shows that a dry mass of 25 g/L is reached after 450 h of culture and an intracellular phycocyanin content of 14 mg/g.

Example 5: Variation in PC Production as a Function of the Gly/Glc Ratio in the Culture Medium A cross-range of glucose and glycerol was performed to evaluate the effect of glycerol on the lifting of inhibition of phycocyanin synthesis related to the presence of glucose in the culture medium. The total amount of organic carbon in each Erlenmeyer flask is 30 g/L. Glucose is symbolized by the contraction "glc" and glycerol by "gly". The concentration of each element in the medium is indicated in Table 3.

PC production according to substrates (mg/gX/h)

| substrate | PC productivity (mg/gX/h) | DM (gX/L) | PC concentration (mg/gX) |
|---|---|---|---|
| 30 g/L Gly | 3.45 | 19.72 | 42.02 |
| 25 Gly/5 Glc | 5.60 | 19.97 | 67.29 |
| 20 Gly/10 Glc | 4.80 | 17.82 | 64.58 |
| 15 Gly/15 Glc | 3.98 | 16.60 | 57.53 |
| 10 Gly/20 Glc | 4.19 | 16.42 | 61.3 |
| 5 Gly/25 Glc | 3.76 | 17.47 | 51.64 |
| 30 g/L Glc | 1.10 | 18.80 | 14.17 |

Example 6: Variation in PC Production as a Function of the Gly/Glc Ratio in the Culture Medium (Glycerol Concentration Less than 5 g/L)

This example complements Example 5, the culture conditions being similar with the only difference in the glycerol concentrations tested which are less than or equal to 5 g/L in order to quantify the limit glycerol concentration to lift the inhibition of phycocyanin synthesis by glucose in the culture medium.

Productivity (mg/g/h)

| substrate | PC productivity (mg/gX/h) | DM (gX/L) | PC concentration (mg/gX) |
|---|---|---|---|
| 30 g Glc | 0.68 | 11.45 | 14.31 |
| 1 g/L Gly/29 Glc | 0.66 | 11.41 | 14 |
| 2 g/L Gly/28 Glc | 0.84 | 11.59 | 17.47 |
| 3 g/L Gly/27 Glc | 0.86 | 11.7 | 17.56 |
| 4 g/L Gly/26 Glc | 1.03 | 11.65 | 21.3 |
| 5 g/L Gly/25 Glc | 1.01 | 11.62 | 20.77 |
| 30 g/L Gly | 1.29 | 12.84 | 24.19 |

Example 7: Variation in PC Production as a Function of the Proportion of Glycerol Supplied in a Medium Containing 30 g/L Milk Permeate at the Beginning of the Culture Different amounts of glycerol are provided to a medium composed of milk permeate in order to observe its effect on the synthesis of phycocyanin and the lifting of the inhibition of lactose (glucose+sucrose) on the production of this pigment. The base medium contains 30 g/L milk permeate. The added glycerol is symbolized by the contraction "gly". Six glycerol concentrations are tested (0, 1, 2, 3, 4 and 5 g/L).

Productivity (mg/L/h)

| glycerol | PC productivity (mg/gX/h) | DM (gX/l) | PC concentration (mg/gX) |
|---|---|---|---|
| 0 g/L | 0.13 | 19.4 | 1.09 |
| 1 g/L | 0.53 | 18.7 | 4.74 |
| 2 g/L | 1.05 | 21 | 8.42 |
| 3 g/L | 1.45 | 21.7 | 11.26 |
| 4 g/L | 1.90 | 19.7 | 16.22 |
| 5 g/L | 2.31 | 17.4 | 22.33 |

Similarly, as described by Stadnichuk et al. (1998), glucose has a limiting effect on the amount of phycocyanin produced by the *Galdieria sulphuraria* strain, with a concentration of less than 15 mg phycocyanin per g dry matter at the end of growth (15 mg PC/g DM). Conversely, the strain having grown in the presence of glycerol alone accumulates about 40 mg PC/g DM, for the same growing time (240 h). With prolongation, the glycerol-grown culture may have accumulated up to 70 mg PC/g DM, while the glucose-grown culture will have a relatively constant amount of PC/g DM over time. In all other cases (glucose-glycerol mixture) the biomass produced and the amount of PC present in the biomass remains constant and even higher than that of glycerol for the same culture time. These values are comprised between 50 and 60 mg PC/g DM, more than three times that found in the biomass of cells grown on glucose alone.

In conclusion, the addition of small amounts of glycerol in the medium lifts the inhibition of PC synthesis related to the presence of glucose in the medium, whether present in the form of a simple sugar (glucose) or a complex sugar (lactose, sucrose, or other . . . ).

This process makes it possible to grow cells using glucose (or a carbon source containing glucose) as the main carbon source, and to use glycerol only as an inducer for PC synthesis and not as the main substrate. Glucose or glucose-containing carbon sources are generally cheaper than glycerol, and generally make it possible to obtain higher growth rates than on glycerol, thus a savings on fermentation costs.

REFERENCES

Carfagna et al., Algal Research 31 (2018) 406-412
Gross et al., Plant cell Physiol. 36 (1995) 633-638;
Jaouen et al., Biotechnology techniques 13 (1999) 877-881
Moon et al., Korean J. Chem. Eng. 31 (2014) 490-495;
Oesterhelt et al., Plant J. 51 (2007) 500-511
Sloth et al., Enzyme and Microbial Technology 38 (2006) 168-175
Stadnichuk et al., Plant Science 136 (1998) 11-23
FR 2 789 399
FR 3 064 635
WO 2017/050917,
WO 2017/050918,
WO 2017/093345
WO 2018/178334

The invention claimed is:

1. A process for production of a phycocyanin-rich biomass, the process comprising:
   (i) cultivating unicellular red algae (URA) in mixotrophic or heterotrophic mode on a culture medium comprising a carbon source, the carbon source comprising glucose, wherein the cultivating comprises a first step of growth to produce biomass and a second step of accumulation of phycocyanin, and wherein glycerol is added in the culture medium, and
   (ii) recovering the biomass,
   wherein the weight ratio of glycerol to carbon source comprising glucose (Gly/Glu) after addition of glycerol is of at least 1/15.

2. The process according to claim 1, wherein the URA is of the genera Cyanidioschyzon, Cyanidium or Galdieria.

3. The process according to claim 1, wherein the carbon source in the culture medium is selected from the group consisting of: glucose, lactose, fructose or glucose-containing polysaccharides, and mixtures thereof.

4. The process according to claim 1, wherein the carbon source is lactose from milk permeate.

5. The process according to claim 1, wherein the culture medium comprises between 0.05 g/L and 200 g/L of the carbon source comprising glucose.

6. The process according to claim 1, wherein the cultivating is in mixotrophic mode, and further comprises continuous or discontinuous illumination.

7. The process according to claim 1, wherein the addition of glycerol to the culture medium is carried out at the beginning of the culture.

8. The process according to claim 1, wherein the weight ratio of glycerol to carbon source comprising glucose (Gly/Glu) is at least 1/14.

9. The process according to claim 1, wherein the weight ratio of glycerol to carbon source comprising glucose (Gly/Glu) is at least 1/10.

10. The process according to claim 1, wherein the weight ratio of glycerol to carbon source comprising glucose (Gly/Glu) is at least 1/5.

11. The process according to claim 1, wherein the weight ratio of glycerol to carbon source comprising glucose (Gly/Glu) is from 1/5 to 1/3.

12. A process for preparing phycocyanins, the process comprising:
(i) cultivating unicellular red algae (URA) in mixotrophic or heterotrophic mode on a culture medium comprising a carbon source, the carbon source comprising glucose, wherein the cultivating comprises a first step of growth to produce biomass and a second step of accumulation of phycocyanin, and wherein glycerol is added in the culture medium,
(ii) recovering the biomass,
wherein the weight ratio of glycerol to carbon source comprising glucose (Gly/Glu) after addition of glycerol is of at least 1/15, and
(iii) extracting the phycocyanins from the biomass.

13. The process according to claim 1, wherein the URA is selected among the species *Cyanidioschyzon merolae* 10D, *Cyanidioschyzon merolae* DBV201, *Cyanidium caldarium*, *Cyanidium daedalum*, *Cyanidium maximum*, *Cyanidium partitum*, *Cyanidium rumpens*, *Galdieria daedala*, *Galdieria maxima*, *Galdieria partita* or *Galdieria sulphuraria*.

14. The process according to claim 1, wherein the addition of glycerol to the culture medium is carried out once the biomass has reached a density greater than 20 g/L dry matter.

15. The process according to claim 1, wherein the biomass recovered has a phycocyanin content of between 1 and 250 mg/g dry matter.

16. The process according to claim 1, wherein the biomass recovered has a phycocyanin content of between 0.5 and 100 mg/g dry matter.

17. The process according to claim 1, wherein the biomass recovered has a carotenoid content between 0.1 and 10 mg/g dry matter.

\* \* \* \* \*